United States Patent [19]

Murai et al.

[11] 4,031,303
[45] June 21, 1977

[54] STERYL-β-D-GLUCOSIDE ESTERS AND METHOD OF PREPARATION

[75] Inventors: Hiromu Murai; Koji Kitaguchi; Tatsuo Suminokura; Akira Sano; Masahiro Kise; Masahiko Kitano; Toshio Tomita, all of Kyoto, Japan

[73] Assignee: Nippon Shinyaku Co., Ltd., Japan

[22] Filed: Aug. 8, 1975

[21] Appl. No.: 603,110

[30] Foreign Application Priority Data
Aug. 14, 1974 Japan .............................. 49-93621
Aug. 14, 1974 Japan .............................. 49-93622

[52] U.S. Cl. .................................. 536/5; 424/182
[51] Int. Cl.$^2$ ....................................... C07G 17/00
[58] Field of Search ................... 260/210.5, 234 R; 424/182; 536/5

[56] References Cited
UNITED STATES PATENTS
3,514,441   5/1970   Satoh et al. .................... 260/210.5

FOREIGN PATENTS OR APPLICATIONS
1,298,047   11/1972   United Kingdom ............ 260/210.5

OTHER PUBLICATIONS
Kiribuchi et al., "Agr. Biol. Chem.", vol. 31, No. 10, pp. 1244–1247, 1967.

Primary Examiner—Johnnie R. Brown

[57] ABSTRACT

Steryl-6-0-palmitoyl-β-D-glucosides are anti-inflammatory agents. The compounds, of which β-sitosteryl-6-0-palmitoyl-β-D-glucoside is a representative embodiment, are prepared through the reaction of a steryl-6-0-sulfonyl-β-D-glucoside with an alkali metal salt of palmitic acid.

4 Claims, No Drawings

STERYL-β-D-GLUCOSIDE ESTERS AND METHOD OF PREPARATION

DETAILED DESCRIPTION

The present invention pertains to steryl-6-0-palmitoyl-β-D-glucosides, their use as anti-inflammatory agents, and methods for their preparation.

The compounds prepared according to the present invention can be diagrammatically depicted by the formula:

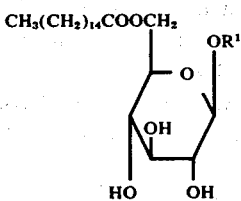

wherein R1 is a steroid group selected from the group consisting of β-sitosteryl, campesteryl, stigmasteryl or cholesteryl.

The foregoing compounds obtained in accordance with this invention exhibit strong anti-inflammatory effects with an exceptionally low toxicity. They are accordingly extremely useful as pharmaceuticals, in particular for use in effecting an anti-inflammatory response in humans and animals through administration of an anti-inflammatorily effective amount of the compound.

The compounds are prepared by treating a 3-(6-sulfonyl-β-D-glucoside) of said steroid with an alkali metal salt of palmitic acid. Suitable salts include the sodium and potassium palmitates. The reaction is preferably conducted in a solvent, as for example N,N-dimethylformamide, ethanol, dioxane, and the like, generally with the application of external heat. The 3-(6-sulfonyl-β-D-glucoside) of the steroid is in turn prepared through the reaction of a steryl-β-D-glucoside with a sulfonyl chloride. The nature of the particular sulfonyl chloride is relatively non-critical and substantially any of the known sulfonyl chlorides can be utilized, as for example p-chlorobenzenesulfonyl chloride; 2,3,5,6-tetramethylbenzenesulfonyl chloride; 2,3,4,5,6-pentamethylbenzenesulfonyl chloride; 2,4,6-trimethylbenzenesulfonyl chloride; 2-methylbenzenesulfonyl chloride; 2-nitrobenzenesulfonyl chloride; benezenesulfonyl chloride; methanesulfonyl chloride; ethanesulfonyl chloride; and the like. Preferably the sulfonyl chloride is of the formula $R^2SO_2Cl$ wherein $R^2$ is alkyl or aryl, in particular methyl, ethyl, phenyl, chloropenyl, nitrophenyl or phenyl substituted by from 1 to 5 methyl groups.

The steryl-β-D-glucosides can be isolated from lecithin according to known methods and are in general commercially available. From an economic point of view, it is particularly attractive to utilize commercially available β-sitosteryl which is approximately 60% in purity and contains the β-D-glucosides of campesterol, stigmasterol and related sterols. Likewise, one may use the commercially available β-D-glucosides of cholesterol, campesterol and the like. It is generally unnecessary to isolate the individual steryl components of these β-D-glucosides and the mixtures may be used as such, both in the preparation of the antiinflammatory product and its eventual use.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to inprove the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The potent anti-inflammatory properties of the present compounds and the exceptionally low toxicity can be conveniently observed in well known and widely accepted laboratory models. For example, the anti-inflammatory properties are apparent in the carrageenin-induced rat paw edema method in which a significant anti-inflammatory effect is observed as much as five hours after intraperitoneal injection of doses as low as 10 mg/kg. The overall pattern of anti-inflammatory effects can be seen from the following data:

Table I

| Inhibitory Effect of Carrageenin-Induce Edema (Paw Edema Method in Rats) | | | | | |
|---|---|---|---|---|---|
| I.P. Dose | % Inhibition | | | | |
| (mg/kg) | 1 hr | 2 hrs | 3 hrs | 4 hrs | 5 hrs |
| 10 | −3.7 | 13.2 | 26.6 | 37.1 | 24.9 |
| 20 | 24.2 | 37.6 | 41.6 | 42.8 | 28.1 |

The $LD_{50}$ in mice for these compounds is greater than 3,000 mg/kg upon either intraperitoneal or oral administration, in both male and female animals.

The following examples will serve to further typify the nature of the present invention but should not be construed as a limitation on the scope thereof, the scope being defined solely by the appended claims.

EXAMPLE 1

Steryl-$\beta$-D-glucoside (23 g) was dissolved in 100 ml of pyridine and 23 g of p-toluenesulfonyl chloride were added thereto with cooling. The reaction mixture was allowed to slowly reach room temperature. Agitation of the mixture was continued for about three hours and then the reaction was terminated by addition of a small amount of methanol. The solvent was removed under reduced pressure and the residue recrystallized from ethanol to give 15 g of steryl-6-0-p-toluenesulfonyl-$\beta$-D-glucoside, m.p. 156°–157° C.

Elementary analysis calculated for $C_{42}H_{66}O_8$ S.½$H_2O$; C 68.16%; H 9.13%; S 4.33%; Found: C 68.15%; H 9.36%; S 4.23%.

Alternatively, the steryl-$\beta$-D-glucoside was allowed to react with various sulfonyl chloride compounds in the same manner as in above. Examples of such sulfonyl chloride compounds used were p-chlorobenzenesulfonyl chloride; 2,3,5,6- tetramethylbenzenesulfonyl chloride; 2,3,4,5,6-pentamethylbenzenesulfonyl chloride; 2,4,6-trimethylbenzenesulfonyl chloride; 2-methylbenzenesulfonyl chloride; 2-nitrobenzenesulfonyl chloride; benzenesulfonyl chloride; and methanesulfonyl chloride. The reaction was traced by thin layer chromatography and the product was isolated from the reaction mixture on the basis of the largest spot. The yields obtained were almost equal to those determined by colorimetric method (based on color developed by sterols). The yield using p-toluenesulfonyl chloride was 50–60% and those with the various other sulfonyl chlorides listed were 50 to 65%.

EXAMPLE 2

The 6-0-p-toluenesulfonyl derivative of Example 1 (1 g) was dissolved in 20 ml of N,N-dimethylformamide, and 0.57 g of pulverized sodium palmitate was added thereto. The mixture was heated with agitation at 120° C for 1.5 hours, and slowly developed color. Upon completion of the reaction, chloroform was added and the insoluble matter was removed by filtration. The filtrate was treated with activated carbon and distilled in vacuo to give 830 mg of crude crystalline material. The crystals were recrystallized from ethanol to give pure desired product, m.p. 120°–190° C.

Analysis calculated for $C_{51}H_{90}O_7$; C 75.13%; H 11.13%; Found: C 74.89%; H 10.90%.

The product can be further purified through chromatography in the conventional manner.

What is claimed is:

1. Process for the preparation of compounds of the formula:

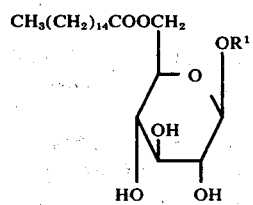

wherein $R^1$ is a steroid group selected from the group consisting of $\beta$-sitosteryl, campesteryl, stigmasteryl or cholesteryl which comprises heating a 3-(6-sulfonyl-$\beta$-D-glucoside) of said steroid with an alkali metal salt of palmitic acid in the presence of a solvent.

2. Process according to claim 1 wherein said 3-(6-sulfonyl-$\beta$-D-glucoside) is of the formula:

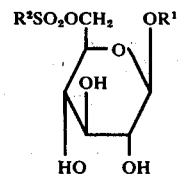

wherein $R^1$ is as therein defined and $R^2$ is methyl, ethyl, phenyl, chlorophenyl, nitrophenyl or phenyl substituted by from 1 to 5 methyl groups.

3. Process according to claim 1 in which a compound of the formula:

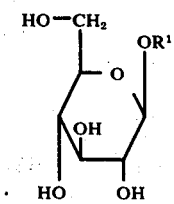

wherein $R_1$ is as therein defined is treated in the presence of a solvent with a compound of the formula $R^2SO_2Cl$ wherein $R^2$ is as therein defined and the resulting 3-(6-sulfonyl-$\beta$-D-glucoside) of said steroid is treated with said alkali metal salt as therein described.

4. A compound of the formula:

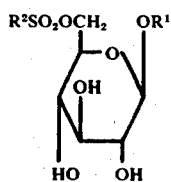
wherein
R[1] is selected from the group consisting of β-sitosteryl, campesteryl, stigmasteryl, and
R[2] is methyl, ethyl, phenyl, chlorophenyl, nitrophenyl or phenyl substituted with from 1 to 5 methyl groups.
* * * * *